United States Patent
Berzak et al.

(10) Patent No.: US 9,039,689 B2
(45) Date of Patent: *May 26, 2015

(54) PHASE SEPARATION OF CRYOGEN IN CRYOSURGICAL INSTRUMENT

(71) Applicant: ICECURE MEDICAL LTD., Caesarea (IL)

(72) Inventors: Nir Berzak, Tel Aviv (IL); Ron Hilleli, Zichron Yaacov (IL)

(73) Assignee: ICECURE MEDICAL LTD., Caesarea (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/547,483

(22) Filed: Nov. 19, 2014

(65) Prior Publication Data

US 2015/0080871 A1 Mar. 19, 2015

Related U.S. Application Data

(63) Continuation-in-part of application No. 14/204,175, filed on Mar. 11, 2014, now Pat. No. 8,906,004, which is a continuation-in-part of application No. 13/232,203, filed on Sep. 14, 2011, now Pat. No. 8,709,005.

(60) Provisional application No. 61/484,822, filed on May 11, 2011.

(51) Int. Cl.
*A61B 18/02* (2006.01)
*A61B 18/00* (2006.01)

(52) U.S. Cl.
CPC ....... *A61B 18/02* (2013.01); *A61B 2018/00577* (2013.01); *A61B 2018/00023* (2013.01); *A61B 2018/0287* (2013.01); *A61B 18/0218* (2013.01); *A61B 2018/0293* (2013.01)

(58) Field of Classification Search
CPC ............... A61B 18/02; A61B 18/0218; A61B 2018/0287
USPC ...................................................... 606/20–26
See application file for complete search history.

(56) References Cited

U.S. PATENT DOCUMENTS

| 3,800,552 A | 4/1974 | Sollami et al. |
| 5,522,870 A | 6/1996 | Ben-Zion |

(Continued)

FOREIGN PATENT DOCUMENTS

WO 2009/128014 10/2009

OTHER PUBLICATIONS

European Patent Office, "International Search Report and Written Opinion of the International Searching Authority received in PCT Application No. PCT/US2011/051529", Jan. 25, 2012.

*Primary Examiner* — Michael Peffley
*Assistant Examiner* — Daniel Fowler
(74) *Attorney, Agent, or Firm* — The Law Office of Michael E. Kondoudis (57) ABSTRACT

A cryosurgical instrument including: a core, a cryogen delivery tube, a cryogen return tube, and a shaft surrounding the core and the tubes. The shaft has a pointed distal end and a proximal end adapted and configured to receive an inflow of cryogen and to exhaust a flow of expanded cryogen. The cryogen delivery tube and the cryogen return tube both have respective helical portions that spiral around the core. The helical portions of the tubes are in fluid tight contact with the core and an inner surface of the shaft. The helical portions of the tubes spiral about the core in an alternating arrangement such that they alternate along a length of the core. The core and the helical portions of the delivery tube and the return tube comprise centrifugal phase separators.

14 Claims, 8 Drawing Sheets

(56) References Cited

U.S. PATENT DOCUMENTS

| | | |
|---|---|---|
| 5,800,487 A | 9/1998 | Mikus et al. |
| 6,235,019 B1 | 5/2001 | Lehmann et al. |
| 6,706,037 B2 | 3/2004 | Zvuloni et al. |
| 6,929,939 B2 | 8/2005 | Lafontaine |
| 2005/0043725 A1* | 2/2005 | Duong et al. ............ 606/23 |
| 2006/0079867 A1* | 4/2006 | Berzak et al. ............ 606/21 |
| 2007/0149957 A1 | 6/2007 | Ross et al. |
| 2007/0149959 A1 | 6/2007 | DeLonzor et al. |
| 2009/0163902 A1 | 6/2009 | DeLonzor et al. |
| 2009/0182320 A1 | 7/2009 | DeLonzor et al. |
| 2010/0057063 A1* | 3/2010 | Arless et al. ............ 606/21 |

* cited by examiner

PHASE SEPARATION OF CRYOGEN IN CRYOSURGICAL INSTRUMENT

CROSS-REFERENCE TO RELATED APPLICATION

This application is a continuation-in-part of U.S. patent application Ser. No. 14/204,175, filed Mar. 11, 2014, now U.S. Pat. No. 8,906,004, which is a continuation-in-part of U.S. patent application Ser. No. 13/232,203, filed Sep. 14, 2011, now U.S. Pat. No. 8,709,055, which claims the benefit of U.S. Provisional Application No. 61/484,822, filed May 11, 2011.

BACKGROUND

1. Technical Field

Embodiments of the present invention relate generally to cryosurgical instruments such as cryoprobes and, more particularly, to phase separation of cryogen in cryosurgical instruments for heat exchanging advantage.

2. Description of Related Art

It is known to employ coiled heat exchangers in cryosurgical instruments with cryogen supplied as a pressurized gas. In such heat exchangers, the expansion of the gas causes it to change its temperature. As explained in U.S. Pat. No. 6,706,037, for example, this phenomenon is referred to as the "Joule-Thomson effect" and is thermodynamically known as adiabatic expansion.

It is also known, in coiled heat exchangers, to use gases that cool upon expansion, such as Argon or Nitrogen, for cooling, and gases that heat as a result of the expansion, such as Helium, for heating. In these heat exchangers, the return gases are commonly used to recycle the thermal energy (i.e., the return cooling gas not only cools the outer surface of the cryosurgical instrument but also the inlet pressurized gas). The coil shape increases the contact area between cool fluids to hot fluids. The heat transfer between these fluids is proportional to the contact surface between them. Thus, the coil serves as an advantageous solution for such heat regeneration. See, for example, U.S. Pat. No. 6,706,037 (at column 15 lines 40-58, and column 16 lines 65-68). Also, as discussed in U.S. Pat. Nos. 3,800,552 and 5,522,870, lowering the inlet temperature may liquefy the expanded gas.

Still further, approaches to enhancing the cooling and heating regeneration are known. For example, U.S. Pat. No. 5,800,487 discusses enhancing the cooling and heating regeneration by supplying the inlet pressurized gas tube with fins to increase the area of the heat exchanging.

If the cryogen is supplied as a liquid or a two-phase (gas/liquid) fluid, cooling methods use the energy required for the change of phase of the inlet cryogen. In this case, the temperature of the inlet fluid and the return fluid may be the same or close in value, and would minimize, or annul heat exchange between the inlet and outlet fluids, due to a small differential temperature. The application of a coil serves as a separator of the phases in a two-phase flow. This is because the liquid phase has greater specific gravity, which tends to cause the liquid phase toward the outer (greater) diameter. The greater diameter of the coil is close to the external surface and, as a result, the boiling or change of phase of the liquid occurs close to the external surface. This arrangement utilizes the physical shape of the coil as a centrifugal force generator to separate the heavier liquid phase from the lighter gaseous phase, forcing (urging) the liquid towards the outer surface of the coil.

When the cryogens, either in gaseous form or two-phase form, enter in a straight delivery tube, or lumen, flow directing elements (such as those described in U.S. Pat. No. 5,800,487) or baffles (such as those described in U.S. Patent Publication No. 2009/0163902 A1, U.S. Patent Publication No. 2007/0149957 A1, U.S. Patent Publication No. 2007/0149959 A1, and U.S. Patent Publication No. 2009/0182320 A1) have been used.

BRIEF SUMMARY

In one aspect, the inventors have discovered a new and novel strategy that yields increased performance of a cryosurgical device by selectively locating the boiling of cryogen in the device. In one exemplary implementation, a cryosurgical instrument includes a coiled tube that serves as both a cryogen delivery tube and a phase separator that separates cryogen into liquid and gaseous phases. A fluid cryogen flows into the coiled tube that, in turn, is in energy exchange contact with the outer wall of a portion of a cryosurgical instrument. The incoming flow spins as it spirals such that it separates into the two phases, with the heaver liquid phase being urged (i.e., forced) into contact with the outer wall of the coil, which is in contact with the outer wall of the cooling zone. This increases the heat exchanging, by boiling, with the outer wall of the cryosurgical instrument. The return tube is an integral part and/or a continuation of the feeding tube In the return flow passage, between the coil and the cylindrical outer surface of the cryosurgical device, the same centrifugal force separate the liquid from the gaseous phase, forcing the liquid towards the outer surface of the external wall of the cryosurgical instrument by centrifugal force. The heat exchange zone comprises at least the distal/downstream tip of the cryosurgical instrument, from the tip of the probe to the insulation, where the fluid is in contact with the outer shaft's inner surface. In this way, the centrifugal force can be advantageously used.

According to another aspect of the present invention, the delivery and the return tubes can be made from square cross section, i.e. generating closed cylinder between the core and the outer shaft.

According to another aspect of the present invention, various parts of the cryosurgical probe are made of flexible materials, allowing the probe to selectively bend by the selective application of force perpendicular to its main axis. The cryogen return tube is extended towards the distal end, and the insulation may be provided by attaching the shaft to vacuum source or pump which maintain vacuum between the shaft or the external tube and the delivery and return tubes.

According to another aspect of the present, the cryogen delivery tube is routed within the return cryogen tube, till the spiral part of it. Since the delivery and the return cryogen are in the state of boiling, there is little, if any exchange of heat between the delivery and the return cryogen.

According to another aspect of the present invention, there is provided a cryosurgical instrument including: a shaft having a closed distal end defining an expansion chamber and an open proximal end adapted and configured (i) to receive an inflow of cryogen and (ii) to exhaust a flow of expanded cryogen; and a heat exchanger. The heat exchanger includes: a solid core element extending along a longitudinal axis of the heat exchanger; and a cryogen delivery tube that spirals around and contacts the solid core element. The spirals of the cryogen delivery tube are spaced from each other and in fluid tight contact with the solid core and an inner surface of the shaft. The cryogen return tube spiral in the gap between the delivery tube, the outer surface of the core, and the inner surface of the shaft, in such way that it can pick heat from the inner surface of the outer shaft, and no gap exist between the delivery and the return tubes.

According to another aspect of the present invention, there is provided a cryosurgical instrument including: a shaft having a closed distal end defining an expansion chamber at which cryogen boils and a proximal end adapted and configured (i) to receive an inflow of cryogen, (ii) deliver the inflow of cryogen to the expansion chamber, and (iii) to exhaust a flow of cryogen that has expanded in the expansion chamber; a solid core element extending along a longitudinal axis of the shaft; and a helical cryogen delivery tube that spirals around the core, is in fluid tight contact with the core, and is in fluid tight contact with an inner surface of the shaft, the respective spirals of the delivery tube being respectively spaced. When spirals of the cryogen delivery tube spin the inflow of cryogen during delivery so as to separate the cryogen into two phases. Also, the spaced spirals of the cryogen delivery tube, the solid core, and an inner surface of the shaft cooperate so as to form a spiraling cryogen exhaust pathway that (i) separates the flow of expanded cryogen flowing from the expansion chamber into two phases, and (ii) urges a heavier liquid phase of the expanded cryogen against a portion of the inner surface of the shaft. In this space, a return tube is placed in such a way that the return flow can either flow within the return tube, open in both end or in the spaced that left free between the return tube and the delivery tube.

According to still another aspect of the present invention, there is provided a cryosurgical instrument having a hollow shaft having a closed distal end forming a tip, the instrument including a phase separator that includes: a solid core element a double threaded type, disposed within the shaft and extending along a longitudinal axis of the shaft; and one thread and the inner wall of the outer shaft serve as the cryogen delivery tube, and the other thread as the cryogen return lumen in such a way that (i) spirals around the longitudinal axis such that the respective spirals are spaced from each other. The respective spirals are in fluid tight contact with the inner surface of the shaft. The spinning causes separation of the flow of the delivered cryogen and the expanded cryogen into a liquid phase and a gaseous phase and urges a heavier liquid phase of the expanded cryogen against a portion of the inner surface of the shaft.

According to still another aspect of the present invention, there is provided a method, including: directing a flow of cryogen to an expansion chamber at a tip end of a shaft of a cryosurgical instrument; permitting cryogen in the expansion chamber to expand and cool at least the tip of the cryosurgical instrument; directing a flow of expanded cryogen into an exhaust pathway so that the flow of expanded cryogen flows away from the tip; and spinning the flow of expanded cryogen. The spinning separates the expanded cryogen into a liquid phase and a gas phase and urges the liquid phase into contact with an inner surface of the shaft.

According to still another aspect of the present invention, there is provided a method, including: directing a flow of cryogen to the tip end of a shaft of a cryosurgical instrument; permitting cryogen in the delivery tube and the return tube to be in tight contact with the shaft and cool at least the cooling zone of the cryosurgical instrument; directing a flow of boiled cryogen in a spinning flow to force the liquid phase toward the heat exchanging zone. The spinning separates the cryogen into a liquid phase and a gas phase and urges the liquid phase into contact with an inner surface of the shaft.

According to still another aspect of the present invention, there is provided a cryosurgical instrument including: a shaft having a pointed distal end and a proximal end adapted and configured to receive an inflow of cryogen and to exhaust a flow of expanded cryogen; a core disposed within the shaft; a cryogen delivery tube having a helical portion that spirals around the core, the delivery tube configured to deliver a received flow of cryogen to a downstream end near the pointed distal end of the shaft; and a cryogen return tube having a helical portion that spirals around the core, the return tube configured to accept, at an upstream end thereof near the distal pointed end of the shaft, a return flow of cryogen. The helical portions of the tubes may be in fluid tight contact with the core and an inner surface of the shaft. The helical portions of the tubes may spiral about the core in an alternating arrangement such that they alternate along a length of the core. The core and the helical portions of the delivery tube and the return tube may comprise a centrifugal phase separator.

According to still another aspect of the present invention, there is provided a cryosurgical instrument including: a shaft having a pointed distal end and a proximal end adapted and configured to receive an inflow of cryogen and to exhaust a flow of expanded cryogen; a core disposed within the shaft; and a cryogen delivery tube having a helical portion that spirals around the core and delivers a flow of cryogen toward the pointed distal end of the shaft, the delivery tube being in fluid tight contact with the core and an inner surface of the shaft; and a cryogen return tube having a helical portion that spirals around the core, the return tube configured to accept, at an upstream end thereof near the distal pointed end of the shaft, a return flow of cryogen.

The respective spirals of the helical portions of the tubes may be respectively spaced. The helical portions may spin a cryogen flowing therethrough so as to promote phase separation of the cryogen. The spaced spirals of the helical portions of the tubes, the core, and the inner surface of the shaft cooperate so as to form a spiraling cryogen return pathway that spins a cryogen flowing therethrough so as to promote phase separation of a flow cryogen therethrough. Expanded cryogen may be exhausted via the return tube or the return pathway.

According to still another aspect of the present invention, there is provided a cryosurgical instrument including: a shaft having a pointed distal end and a proximal end adapted and configured to receive an inflow of cryogen and to exhaust a flow of expanded cryogen; and a core disposed within the shaft and in fluid tight contact with an inner surface of the shaft, the core having two exterior spiraling threads that cooperate with the inner surface of the shaft to form first and second respective spiraling pathways, a first spiraling pathway being a cryogen delivery pathway, the second spiraling pathway being a cryogen return pathway. The cryogen delivery pathway may be configured to deliver a received flow of cryogen to a downstream end near the pointed distal end. The cryogen return pathway may be configured to accept, at an upstream end thereof, a return flow of cryogen from the distal pointed end.

The aforementioned and/or other features, aspects, details, utilities, and advantages of the present invention are: set forth in the detailed description which follows and/or illustrated in the accompanying drawings; possibly inferable from the detailed description and/or illustrated in the accompanying drawings; and/or learnable by practice of the present invention.

This Summary is provided to introduce a selection of concepts in a simplified form that are further described below in the Detailed Description. This Summary is neither intended to identify key features or essential features of the claimed subject matter, nor should it be used to limit the scope of the claimed subject matter. Furthermore, the claimed subject matter is not limited to implementations that solve any disadvantage noted in any part of this application.

BRIEF DESCRIPTION OF THE DRAWINGS

The present invention will be more readily understood from the detailed description of embodiments thereof made in conjunction with the accompanying drawings of which.

Like reference numerals refer to like parts throughout the various views unless otherwise specified.

DETAILED DESCRIPTION

Reference will now be made in detail to embodiment(s) of the present invention, examples of which is/are illustrated in the accompanying drawings, wherein like reference numerals refer to the like elements throughout. The embodiment(s) is/are described below to explain the present invention by referring to the figures.

Although the following text sets forth a detailed description of at least one embodiment or implementation, it is to be understood that the legal scope of protection of this application is defined by the words of the claims set forth at the end of this disclosure. The detailed description is to be construed as exemplary only and does not describe every possible embodiment since describing every possible embodiment would be impractical, if not impossible. Numerous alternative embodiments and/or implementations are both contemplated and possible, using either current technology or technology developed after the filing date of this patent, which would still fall within the scope of the claims.

It is to be understood that, unless a term is expressly defined in this application using the sentence "As used herein, the term" is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term is limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

As used herein, the term centrifugal force refers to the tendency of a flow following a curved path to be urged away from the center of curvature due to inertia. Centrifugal force is referred to as a force for convenience and ease of explanation. This centrifugal force urges the liquid phase of two-phase flow following a curved path to be urged away from the center of curvature due to greater specific gravity than the gaseous phase.

Figure 1:
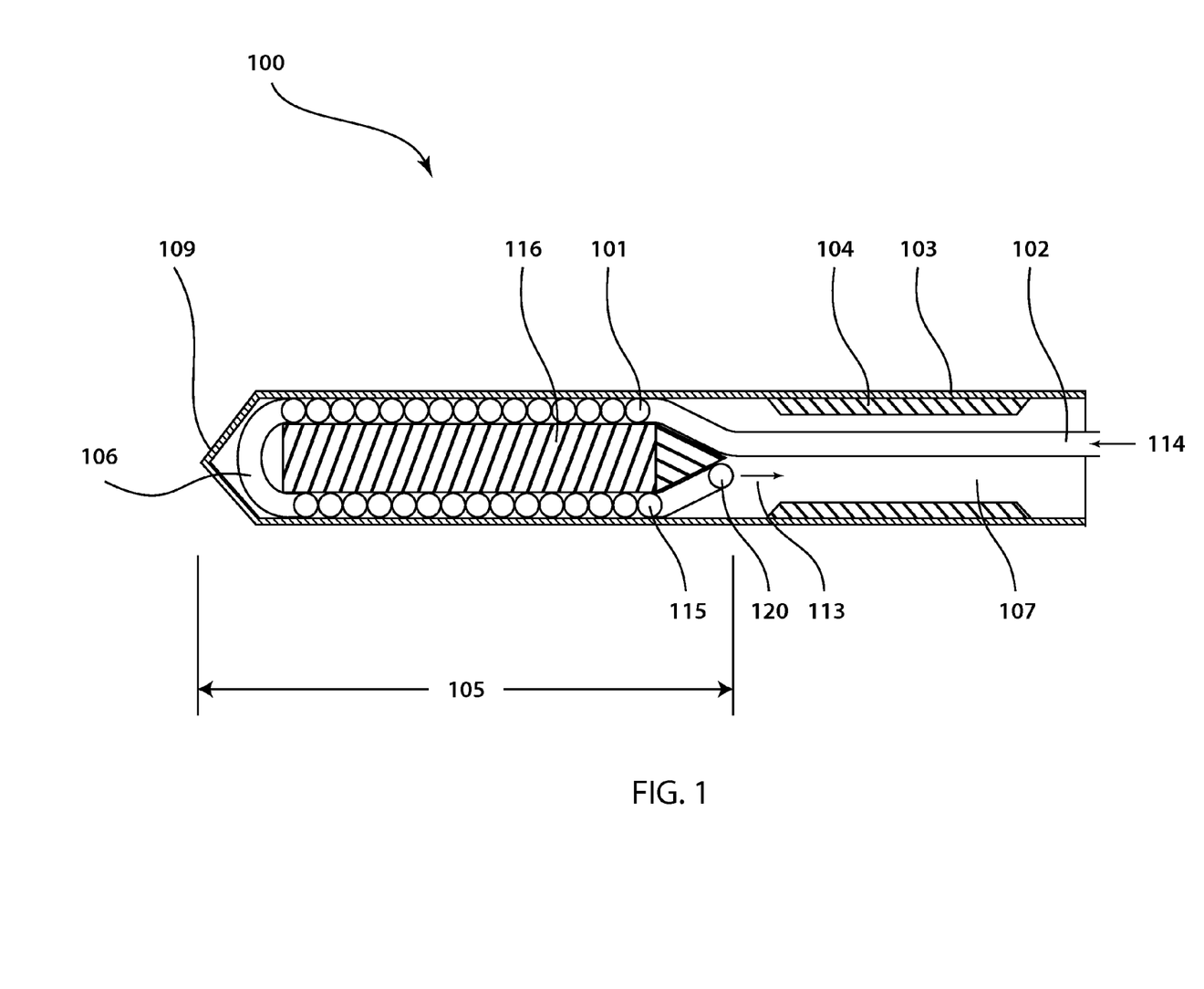
FIG. 1 is cross-sectional view of a non-limiting example of a cryosurgical instrument consistent with an exemplary embodiment of the present invention.

Referring to FIG. 1, there is shown a non-limiting example of a cryosurgical instrument comprising a heat exchanger that features multiple helical coils, which is consistent with an exemplary embodiment of the present invention.

As shown, the cryosurgical instrument 100 includes a shaft 103 surrounding a core 116, a cryogen delivery tube 101, and a cryogen return tube 115. The cryosurgical instrument 100 also includes a tip 109 at the forward end. The shaft 103 and the tip 109 generally define the exterior of the cryosurgical instrument 100.

At rear portion, the cryosurgical instrument 100 includes insulation 104 located on an internal surface of the external shaft 103. The insulation 104 separates the inner surface of the shaft 103 from a return flow 113 of cryogen exiting the cryosurgical instrument 100 so as to reduce any heat transfer therebetween. The rear portion also includes a cryogen inlet 102 through which cryogen is received by the cryogen delivery tube 101 and is then directed toward the tip 109.

The portion of the cryosurgical instrument from the tip 109 to the insulation 104 defines a cooling zone 105. This cooling zone 105 is a zone in which heat is exchanged between the cryogen and the cryoprobe. As a result, the freezing (ablation) of tissue occurs around the cooling zone 105, when the instrument is in operation and in contact with tissue.

As explained above, the shaft 103 features insulation 104 that is mounted to the inner surface of the shaft 103. The insulation 104 is disposed outside of the cooling (heat exchange) zone 105. The presence of the insulation 104 ensures that freezing occurs only where treatment is desired, which is generally around the cooling zone 105.

The core 116 is disposed lengthwise along a longitudinal or lengthwise axis of the cryosurgical instrument. For this reason, it is preferable that the core has a substantially cylindrical shape with a substantially circular cross-section. It is to be understood, however, that other cross-sectional shapes are both possible and contemplated. Also, it is preferable that the outside diameter of the core 116 and the inner diameter of the shaft 103 are respectively uniform, so that the space between the core 116 and the shaft 103 is uniform. It is to be understood, however, that other shapes and non-uniform diameters are both possible and contemplated.

The inlet 102 is configured to receive a flow of cryogen and the cryogen delivery tube 101 delivers the received cryogen into the shaft 103. The cryogen delivery tube 101 and the cryogen return 115 are arranged so as to substantially surround the core 116. To this end, the delivery tube 101 includes a helical portion that spirals around the core 116 from a distal end of the core 116 (relative to the tip 109) to a proximal end near the tip 109. The delivery tube 101 terminates at a bend 106 near the tip 109. At the bend 106, the delivery tube 101 transitions into the return tube 115 and changes direction by 180 degrees. The return tube 115 includes a helical portion that spirals around the core 116 from a proximal end of the core 116 (relative to the tip 109) away from the tip 109.

It is preferable that the delivery tube 101 and the return tube 115 fit tightly between the core 116 and the shaft 103 so that the tubes are in direct contact with the shaft 103. This tight fit promotes temperature communication between the tubes and the shaft 103 in the cooling zone 105. To encourage the tight fit, it is preferably that the delivery tube 101 and the return tube 115 share the same, uniform outside diameter. It is to be understood, however, that the diameters need not be uniform or even the same. Further, it is to be understood that other shapes of the tubes are both possible and contemplated.

It is to be appreciated that the helical portions of both the delivery tube 101 and the return tube 115 contemporaneously spiral around the core 116 in a cooperative manner such that respective windings of these helical portions alternate, when the cryosurgical instrument 100 is viewed in cross-section as in FIG. 1. As a result, in operation, the respective windings interweave around the core 116 and provide two cryogen phase separators, as explained below. Also, the delivery tube 101 and the return tube 115 are in contact with the inner surface of the shaft 103 in at least the cooling zone 105. This results in effective temperature communication between the tubes and the shaft 103.

Operation of the cryosurgical instrument 100 is discussed.

In operation, a flow of cryogen enters the delivery tube 101 through the inlet 102, as indicated by arrow 114, and is directed toward the tip 109. This inflow of cryogen flows into and through the helical portion of the delivery tube 101 such that it spirals around the core 116 as it travels toward the tip 109. This spinning of the inflowing cryogen causes the cryogen to at least partially separate into a liquid phase and a gaseous phase, with the heavier liquid phase tending to displace the gaseous phase along the inner surface of the delivery tube 101. As explained above, the delivery tube 101 terminates at a connected bend 106 where the flow of cryogen changes direction by 180 degrees. The return flow, indicated by arrow 113, then flows in the helical portion of the return tube 115, where it spins in the same manner as in the delivery tube. This spinning of the exhaust cryogen further encourages the cryogen to separate into a liquid phase and a gaseous phase, with the heavier liquid phase tending to displace the gaseous phase along the inner surface of the return tube 115.

Thus, in operation, cryogen flows in the delivery tube 101, continues directly to return tube 115 via the bend 106, and leaves the cooling zone 105 to flow out of opening 120 as shown by arrow 113. Bend 106 is optionally placed close to the inner surface of tip 109. It is to be understood, however, that the tip 109 need not be hollow. Also, it is to be appreciated that in some applications, it is advantageous to locate the bend 106 as close as possible to the inner surface of the tip 109.

More specifically, the inflowing cryogen (indicated by arrow 114) boils continuously as it flows in the delivery tube 101, the bend 106, and the return tube 115 until it reaches opening 120. The return flow of exhausted cryogen leaves the cooling zone 105 and continues as the return flow 113, as shown, into a return gap 107. The exhausted cryogen then exits through a cryogen exhaust outlet (not shown).

Figure 2:
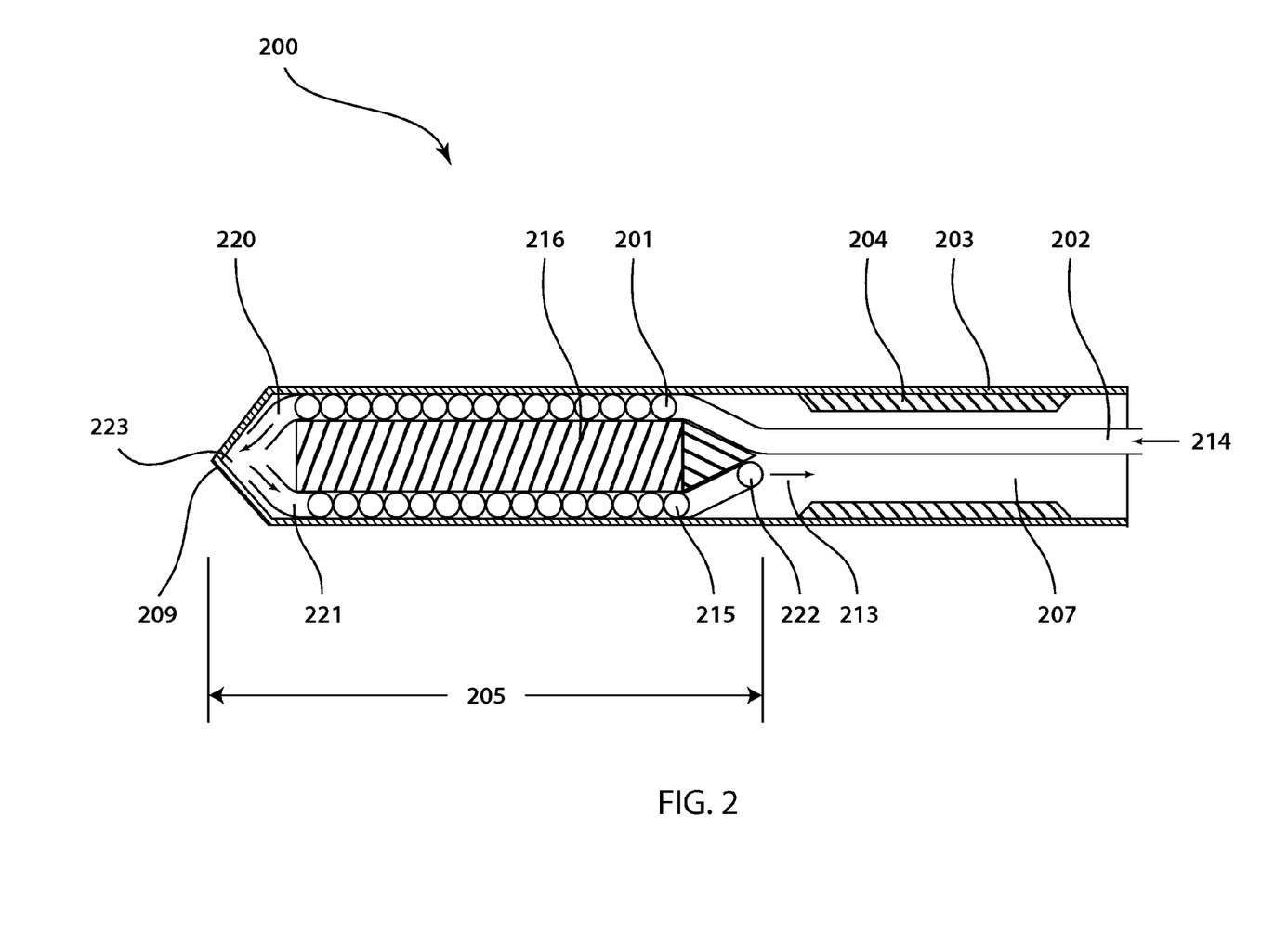
FIG. 2 is cross-sectional view of a non-limiting example of a cryosurgical instrument consistent with an exemplary embodiment of the present invention.

Referring now to FIG. 2, there is illustrated a cross-sectional view of another non-limiting example of a cryosurgical instrument 200 consistent with an exemplary embodiment of the present invention.

Generally, the cryosurgical instrument 200 comprises a heat exchanger that features multiple helical coils, which is consistent with an exemplary embodiment of the present invention. The cryosurgical instrument 200 differs from the cryosurgical instrument 100 of FIG. 1 in that the cryosurgical instrument 200 does not include a bend between the delivery tube 201 and the return tube 215. Instead, the cryosurgical instrument includes an expansion chamber 223.

As shown, the cryosurgical instrument 200 includes a shaft 203 surrounding a core 216, a cryogen delivery tube 201, and a cryogen return tube 215. The cryosurgical instrument 200 also includes a tip 209 at the forward end of the cryosurgical instrument 200. The shaft 203 and the tip 209 generally define the exterior of the cryosurgical instrument 200.

At the rear portion, the cryosurgical instrument 200 includes insulation 204 located on an internal surface of the external shaft 203. The insulation 204 separates the inner surface of the shaft 203 from a return flow 213 of cryogen exiting the cryosurgical instrument 200 so as to reduce any heat transfer therebetween. The rear portion also includes a cryogen inlet 202 through which cryogen enters the cryogen delivery tube 201 and is delivered toward the tip 209.

At the front portion within the tip 209, the cryosurgical instrument 200 includes an expansion space 223. The expansion space 223 receives cryogen from the delivery tube 201 and permits received cryogen to expand. This expansion, in turn, promotes boiling of the cryogen. The boiling that occurs in the expansion space cools the tip 209 as heat energy is absorbed from the tissue by the expanding cryogen.

The portion of the cryosurgical instrument from the tip 209 to the insulation 204 defines a cooling zone 205. This cooling zone 205 is a zone in which heat is exchanged between the cryogen and the cryoprobe. As a result, the freezing (ablation) of tissue occurs around the cooling zone 205, when the instrument is in operation and in contact with tissue.

As explained above, the shaft 203 features insulation 204 that surrounds the shaft 203 and is mounted to the inner surface of the shaft 203. The insulation 204 is disposed outside of the cooling (heat exchange) zone 205. The presence of the insulation 204 ensures that freezing occurs only where treatment is desired, which is generally around the cooling zone 205.

The core 216 is disposed lengthwise along a longitudinal or lengthwise axis of the cryosurgical instrument. For this reason, it is preferable that the core has a substantially cylindrical shape with a substantially circular cross-section. It is to be understood, however, that other cross-sectional shapes are both possible and contemplated. Also, it is preferable that the outside diameter of the core 216 and the inner diameter of the shaft 203 are respectively uniform, so that the space between the core 216 and the shaft 203 is uniform. It is to be understood, however, that other shapes and non-uniform diameters are both possible and contemplated.

The inlet 202 is configured to receive a flow of cryogen and the cryogen delivery tube 210 delivers the received cryogen into the shaft 103. The cryogen delivery tube 201 and the cryogen return tube 215 are arranged so as to substantially surround the core 216. To this end, the delivery tube 201 includes a helical portion that spirals around the core 216 from a distal end of the core 216 (relative to the tip 209) to a proximal end near the tip 209. The delivery tube 201 ends at the tip 209, discharging the cryogen into at an expansion chamber 223 through opening 220. From the expansion chamber the return tube 215 receives cryogen via opening 221 and carries the cryogen to its opening 222. Like the delivery tube 201, the return tube 215 includes a helical portion that spirals around the core 216 from a proximal end of the core 216 (relative to the tip 209) away from the tip 209. The helical portion spins cryogen in the same manner as the delivery tube 201. The cryogen exiting opening 222 flows out of the shaft 203 as indicated by exhaust flow 213.

It is preferable that the helical portions of both the delivery tube 201 and the return tube 215 fit tightly between the core 216 and the shaft 203 so that the helical portions of the tubes are in direct contact with the shaft 203. This tight fit promotes temperature communication between the tubes and the shaft 203 in the cooling zone 205. To encourage the tight fit, it is preferably that the delivery tube 201 and the return tube 215 share the same, uniform outside diameter. It is to be understood, however, that the diameters need not be uniform or even the same. Further, it is to be understood that other shapes of the tubes are both possible and contemplated.

It is to be appreciated that the helical portions of both the delivery tube 201 and the return tube 215 contemporaneously spiral around the core 216 in a cooperative manner such that respective windings of these helical portions of the tubes alternate, when the cryosurgical instrument 200 is viewed in cross-section as in FIG. 2. As a result, in operation, the respective windings interweave around the core 216 and provide two cryogen phase separators, as explained below. Also, the delivery tube 201 and the return tube 215 are in contact with the inner surface of the shaft 203 in at least the cooling zone 205. This promotes enhanced temperature communication between the tubes and the shaft 203.

Operation of the cryosurgical instrument 200 is discussed.

In operation, cryogen enters the delivery tube 201 through the inlet 202, as indicated by arrow 214, and is directed toward the tip 2019. This inflow of cryogen flows into that through the helical portion of the delivery tube 201 such that it spirals around the core 216 as it travels toward the tip 209. This spinning of the inflowing cryogen causes the cryogen to at least partially separate into a liquid phase and a gaseous phase, with the heavier liquid phase tending to displace the gaseous phase along the inner surface of the delivery tube 201. As explained above, the delivery tube 201 delivers the cryogen to the tip 209. The return tube 215, and the cryogen flow into the gap between the insulation 204 and the delivery tube 201 from the opening 220. The return/exhausted flow, indicated by arrow 213, flows in the return tube 215. This spinning of the exhaust cryogen further encourages the cryogen to separate into a liquid phase and a gaseous phase, with the heavier liquid phase tending to displace the gaseous phase along the inner surface of the return tube 215.

Thus, in operation, cryogen flows into the delivery tube 201, spirals abound the core 216, and flows to the tip 209 where it is delivered to the expansion space 223 and permitted to boil further. Thereafter, the expanded cryogen flows into the return tube 215, spirals about the core 216, leaves the cooling zone 205 to flow out of opening 222 as shown by arrow 213.

More specifically, the inflowing cryogen (indicated by arrow 214) boils continuously as it flows in the delivery tube 201, the expansion space 223, and the return tube 215 until it reaches opening 222. The return flow of exhausted cryogen leaves the cooling zone 205 and continues as the return flow 213, as shown, into a return gap 207. The exhausted cryogen then exits through a cryogen exhaust outlet (not shown).

Figure 3:
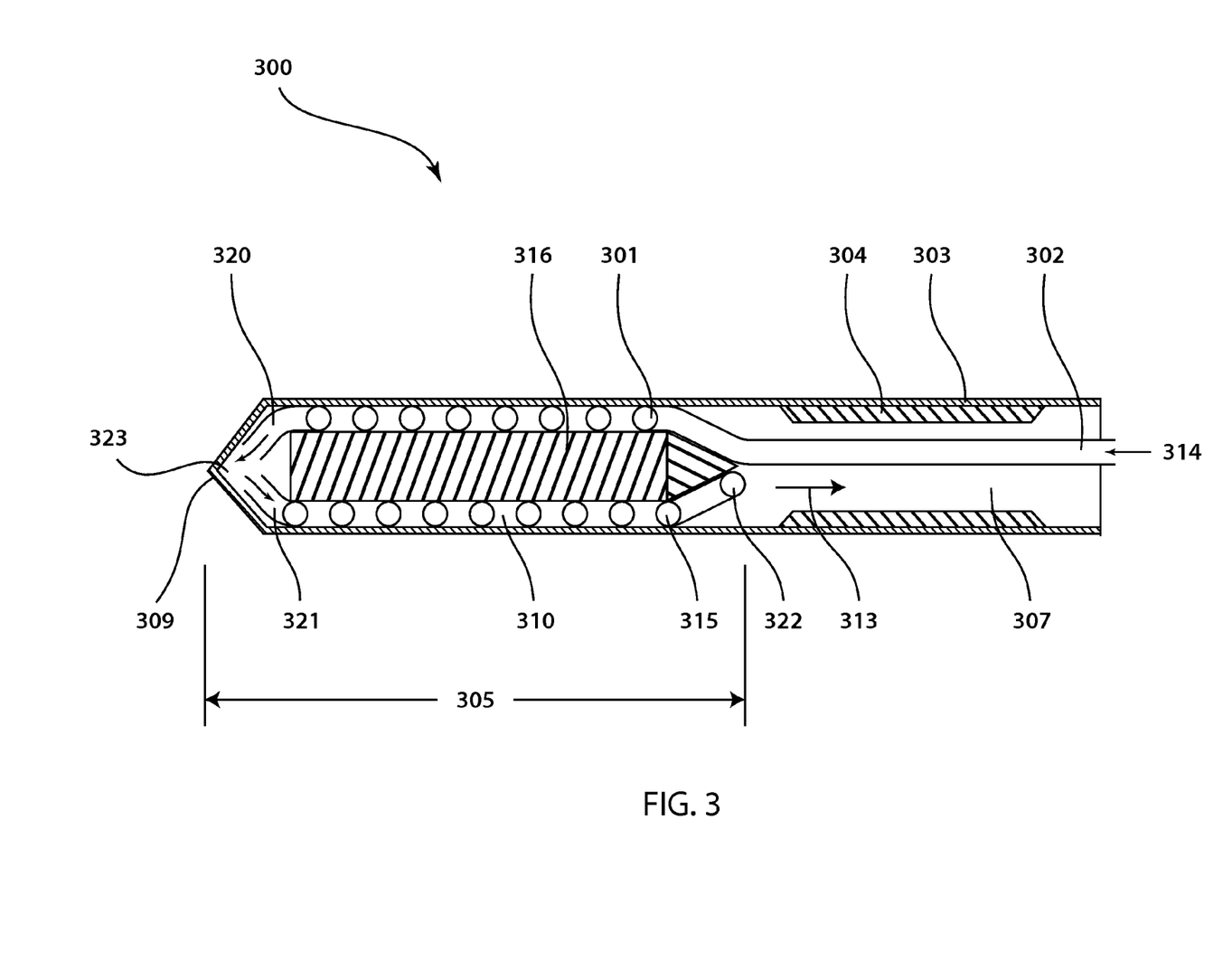
FIG. 3 is cross-sectional view of a non-limiting example of a cryosurgical instrument consistent with an exemplary embodiment of the present invention.

Referring now to FIG. 3, there is illustrated a cross-sectional view of another non-limiting example of a cryosurgical instrument 300 consistent with an exemplary embodiment of the present invention.

Generally, the cryosurgical instrument 300 comprises a heat exchanger that features multiple helical coils, which is consistent with an exemplary embodiment of the present invention. The cryosurgical instrument 300 differs from the cryosurgical instrument 200 of FIG. 2 in that the respective spirals of the helical portions of the delivery tube 301 and the return tube 315 are spaced so that a spiraling (helical) gap 310 results. This gap 310 can receive expanded cryogen from an expansion space 323, as explained in detail below.

As shown, the cryosurgical instrument 300 includes a shaft 303 surrounding a core 316, a cryogen delivery tube 301, and a cryogen delivery tube 315. The cryosurgical instrument also includes a tip 309 at the forward end of the cryosurgical instrument 300. The shaft 303 and the tip 309 generally define the exterior of the cryosurgical instrument 300.

At a rear portion, the cryosurgical instrument 300 includes insulation 304 located on an internal surface of the external shaft 303. The insulation 304 separates the inner surface of the shaft 303 from a return flow 313 of cryogen exiting the cryosurgical instrument 300 so as to reduce any heat transfer therebetween. The rear portion also includes a cryogen inlet 302 through which cryogen enters the cryogen delivery tube 301 and is then delivered toward the tip 309.

The portion of the cryosurgical instrument from the tip 309 to the insulation 304 defines a cooling zone 305. This cooling zone 305 is a zone in which heat is exchanged between the cryogen and the cryoprobe. As a result, the freezing (ablation) of tissue occurs around the cooling zone 305, when the instrument is in operation and in contact with tissue.

The inlet 302 receives cryogen and delivers the received cryogen into the delivery tube 301. As explained above, the shaft 303 features insulation 304 that surrounds the shaft 303 and is mounted to the inner surface of the shaft 303. The insulation 304 is disposed outside of the cooling (heat exchange) zone 305. The presence of the insulation 304 ensures that freezing occurs only where treatment is desired, which is generally around the cooling zone 305.

The core 316 is disposed lengthwise along a longitudinal or lengthwise axis of the cryosurgical instrument. For this reason, it is preferable that the core has a substantially cylindrical shape with a substantially circular cross-section. It is to be understood, however, that other cross-sectional shapes are both possible and contemplated. Also, it is preferable that the outside diameter of the core 316 and the inner diameter of the shaft 303 are respectively uniform, so that the space between the core 316 and the shaft 303 is uniform. It is to be understood, however, that other shapes and non-uniform diameters are both possible and contemplated.

The delivery tube 301 includes a helical portion that spirals around the core 316 from a distal end of the core 316 (relative to the tip 309) to the tip 309. The delivery tube 301 discharges the cryogen near the tip 309, which defines an expansion space or chamber 323. From the expansion chamber 323, the return tube 315 receives cryogen via opening 321 and carries the exhausted cryogen to the opening 322 where it is exhausted via into the return gap 307 via opening 322.

It is preferable that the helical portions of delivery tube 301 and the return tube 315 fit tightly between the core 316 and the shaft 303 so that the tubes are in direct contact with the shaft 303. This spacing fit promotes temperature communication between the tubes and the shaft 303 in the cooling zone 305. It is to be understood, however, that the diameters need not be uniform or even the same. Further, it is to be understood that other shapes of the tubes are both possible and contemplated.

As illustrated in FIG. 3, the respective spirals of the delivery tube 301 and the return tube 315 are spaced, which results in a gap 310. This gap 310, like the helical portions of tubes 301 and 315, spirals around the core 316. This gap 310 can receive expanded cryogen from the expansion space 323, and alone or in cooperation with the return tube 315, deliver expanded cryogen to return gap 307. This arrangement, the inventors have discovered, promotes enhanced the flow of cryogen in the instrument, which is desirable.

It is to be appreciated that the helical portion of the delivery tube 301, the helical portion of the return tube 315, and the gap 310, contemporaneously spiral around the core 316 in a cooperative manner such that respective windings of these tubes alternate, when the cryosurgical instrument 300 is viewed in cross-section as in FIG. 3. As a result, in operation, the respective windings interweave around the core 316 and provide three cryogen phase separators, as explained below. Also, cryogen flowing in the gap 310, the delivery tube 301 and the return tube 315 are in contact with the inner surface of the shaft 303 in at least the cooling zone 305. This results in effective temperature communication between the tubes and the shaft 303.

In operation, cryogen enters through the delivery inlet 302, as indicated by arrow 314, and is directed to delivery tube 301. This inflowing of cryogen then enters the helical portion of the delivery tube 301 and flows in that helical tube such that it spirals around the core 316 as it travels toward the tip 309. This spinning of the inflowing cryogen causes the cryogen to at least partially separate into a liquid phase and a gaseous phase, with the heavier liquid phase tending to displace the gaseous phase along the inner surface of the delivery tube 301. As explained above, the delivery tube 301 discharges the cryogen through opening 320 into the expansion space 323. After the cryogen in the expansion space 323 expands (boils), it flows into one or both of the return tube 315 and the gap 310 between the tubes 301 and 315 until it reaches the return gap 307 between the insulation 304 and the delivery tube 301 where it is exhausted as indicated by arrow 313. This spinning of the exhaust cryogen further encourages the cryogen to separate into a liquid phase and a gaseous phase, with the heavier liquid phase tending to displace the gaseous phase along the inner surface of the return tube 315, and the gap 310.

More specifically, the inflowing cryogen (indicated by arrow 314) boils continuously as it flows in the delivery tube 301, in the expansion chamber 323, and the return tube 315 until it reaches opening 322. The return flow of exhausted cryogen leaves the cooling zone 305 and continues as the return flow 313, as shown, into a return gap 307. The exhausted cryogen then exits through a cryogen exhaust outlet (not shown).

Figure 4:
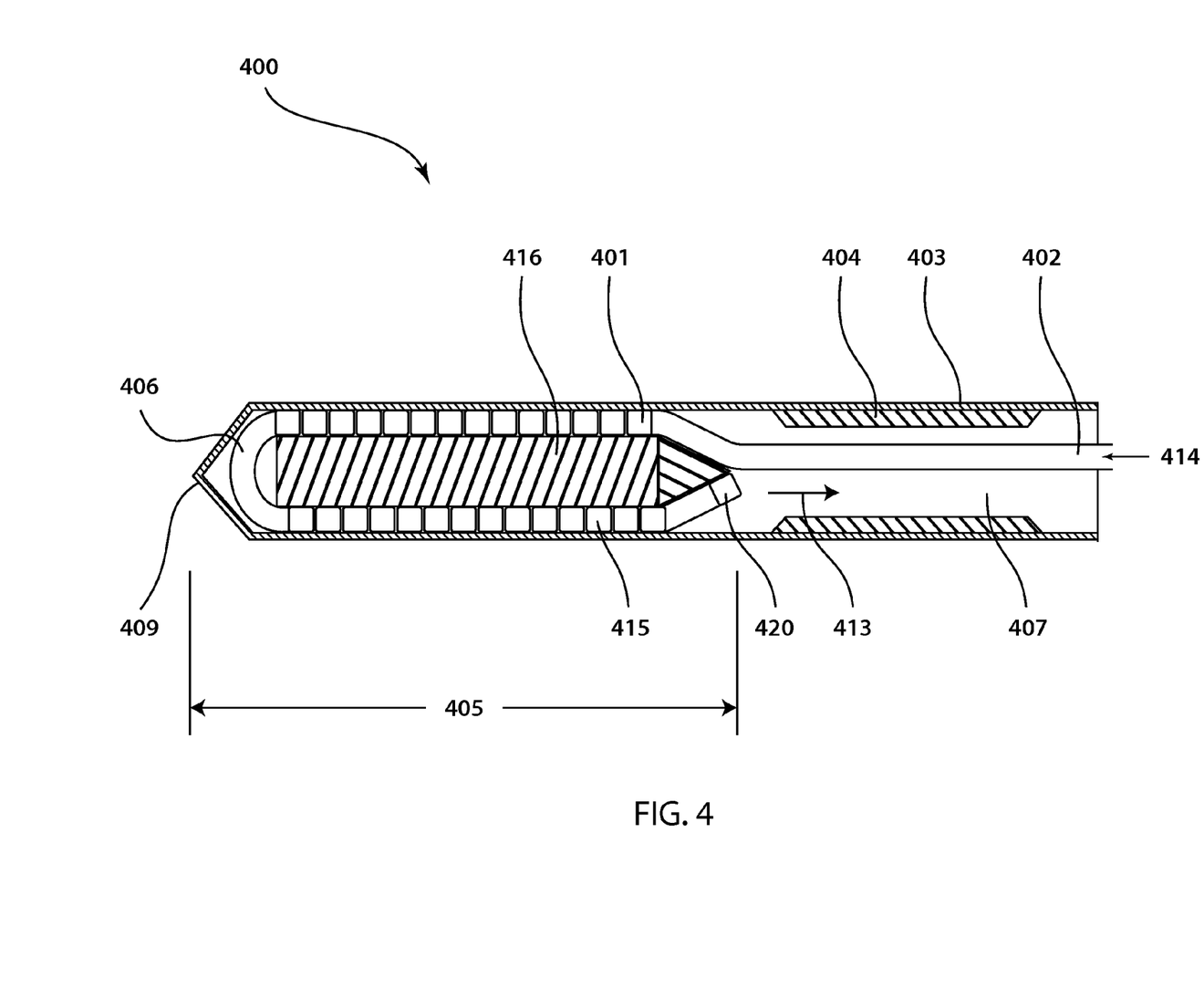
FIG. 4 is cross-sectional view of a non-limiting example of a cryosurgical instrument consistent with an exemplary embodiment of the present invention.

Referring to FIG. 4, there is shown still another non-limiting example of a cryosurgical instrument 400 that is consistent with an exemplary embodiment of the present invention.

Generally, the cryosurgical instrument 400 differs from the cryosurgical instrument 100 of FIG. 1 in that the delivery tube 401 and the return tube 415 both have a square (angular) cross-section. Generally, the cryosurgical instrument 100 comprises a heat exchanger that features multiple helical coils, which is consistent with an exemplary embodiment of the present invention.

As shown, the cryosurgical instrument 400 includes a shaft 403 surrounding a core 416, a cryogen delivery tube 401, and a cryogen return tube 415. The cryosurgical instrument also includes a tip 409 at the forward end of the cryosurgical instrument 400. The shaft 403 and the tip 409 generally define the exterior of the cryosurgical instrument 400.

At rear portion, the cryosurgical instrument 400 includes insulation 404 located on an internal surface of the external shaft 403. The insulation 404 separates the inner surface of the shaft 403 from a return flow 413 of cryogen exiting the cryosurgical instrument 400 so as to reduce any heat transfer therebetween. The rear portion also includes a cryogen inlet 402 through which cryogen is received into delivery tube 401 and then directed toward the tip 409.

The portion of the cryosurgical instrument from the tip 409 to the insulation 404 defines a cooling zone 405. This cooling zone 405 is a zone in which heat is exchanged between the cryogen and the cryoprobe. As a result, the freezing (ablation) of tissue occurs around the cooling zone 405, when the instrument is in operation and in contact with tissue.

As explained above, the shaft 403 features insulation 104 is mounted to the inner surface of the shaft 403. The insulation 404 is disposed outside of the cooling (heat exchange) zone 405. The presence of the insulation 404 ensures that freezing occurs only where treatment is desired, which is generally around the cooling zone 405.

The core 416 is disposed lengthwise along a longitudinal or lengthwise axis of the cryosurgical instrument. For this reason, it is preferable that the core has a substantially cylindrical shape with a substantially circular cross-section. It is to be understood, however, that other cross-sectional shapes are both possible and contemplated. Also, it is preferable that the outside diameter of the core 416 and the inner diameter of the shaft 403 are respectively uniform, so that the space between the core 416 and the shaft 403 is uniform. It is to be understood, however, that other shapes and non-uniform diameters are both possible and contemplated.

The inlet 402 is configured to receive a flow of cryogen and the cryogen delivery tube 401 delivers the received cryogen into the shaft 403. The cryogen delivery tube 401 and the cryogen return tube 415 are arranged so as to substantially surround the core 416. To this end, the delivery tube 401 includes a helical portion that spirals around the core 416 from a distal end of the core 416 (relative to the tip 409) to a proximal end near the tip 409. The delivery tube 401 terminates at a bend 406 near the tip 409. At the bend 406, the delivery tube 401 transitions into the return tube 415 and the flow of cryogen changes direction by 180 degrees.

It is preferable that the helical portions of the delivery tube 401 and the return tube 415 fit tightly between the core 416 and the shaft 403 so that the tubes are in direct contact with the shaft 403. This tight fit promotes temperature communication between the tubes and the shaft 403 in the cooling zone 405. To encourage the tight fit, it is preferably that the delivery tube 401 and the return tube 415 share the same, uniform squared cross-section. It is to be understood, however, that the square cross-section need not be square. Rather other rectangular cross-sections are both possible and contemplated.

It is to be appreciated that both the helical portions of both delivery tube 401 and the return tube 415 contemporaneously spiral around the core 416 in a cooperative manner such that respective windings of these helical portions alternate, when the cryosurgical instrument 400 is viewed in cross-section as in FIG. 4. As a result, in operation, the respective windings interweave around the core 416 and provide two cryogen phase separators, as explained below. Also, the delivery tube 401 and the return tube 415 are in contact with the inner surface of the shaft 403 in at least the cooling zone 405. This results in effective temperature communication between the tubes and the shaft 403.

Operation of the cryosurgical instrument 400 is discussed.

In operation, cryogen enters into the delivery tube 401 through the delivery 402, as indicated by arrow 414, and is directed toward the tip 409. This inflow of cryogen flows into and through the helical portion of the delivery tube such that it spirals around the core 416 as it travels toward the tip 409. This spinning of the inflowing cryogen causes the cryogen to at least partially separate into a liquid phase and a gaseous phase, with the heavier liquid phase tending to displace the gaseous phase along the inner surface of the delivery tube 401. As explained above, the delivery tube 401 terminates at bend 406, where the flow of cryogen changes direction 180 degrees. The return flow, indicated by arrow 413, then flows in the helical portion of the return tube 415, where it spins in the same manner as in the delivery tube. This spinning of the exhaust cryogen further encourages the cryogen to separate into a liquid phase and a gaseous phase, with the heavier liquid phase tending to displace the gaseous phase along the inner surface of the return tube 415.

Thus, in operation, cryogen flows in the delivery tube 401, continues directly to return tube 415 via the bend 406, and leaves the cooling zone 405 to flow out of opening 420 as shown by arrow 413. Bend 406 is optionally placed close to the inner surface of tip 409. It is to be understood, however, that the tip 409 need not be hollow. Also, it is preferable that the bending 406 of the delivery tube 401 be as close as possible to the inner surface of the tip 409.

More specifically, the inflowing cryogen (indicated by arrow 414) boils continuously as it flows in the delivery tube 401, the bend 406, and the return tube 415 until it reaches opening 420. The return flow of exhausted cryogen leaves the cooling zone 405 and continues as the return flow 413, as shown, into a return gap 407. The exhausted cryogen then exits through a cryogen exhaust outlet (not shown).

Figure 5A:
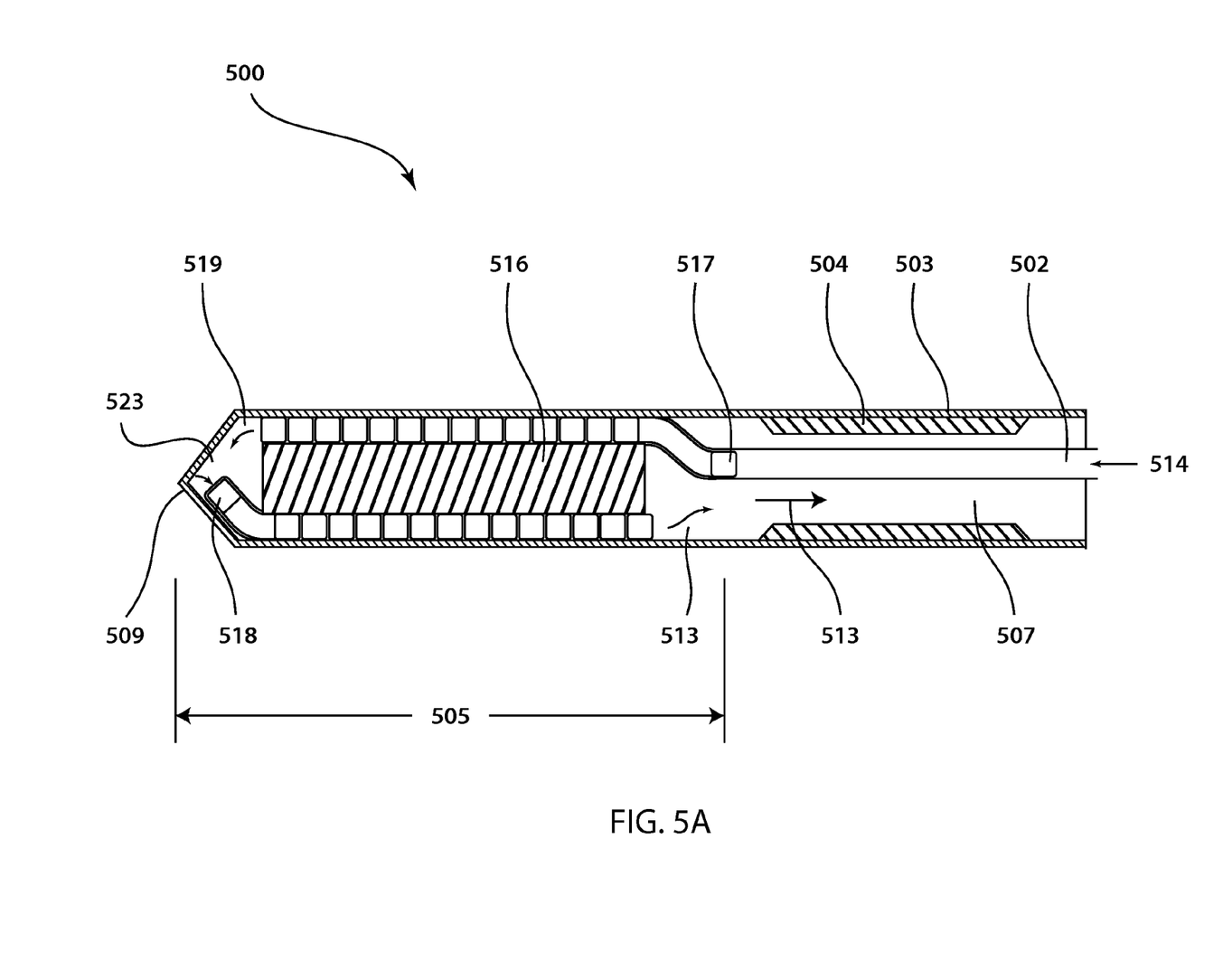
FIG. 5A is cross-sectional view of a non-limiting example of a cryosurgical instrument consistent with an exemplary embodiment of the present invention.
Figure 5B:
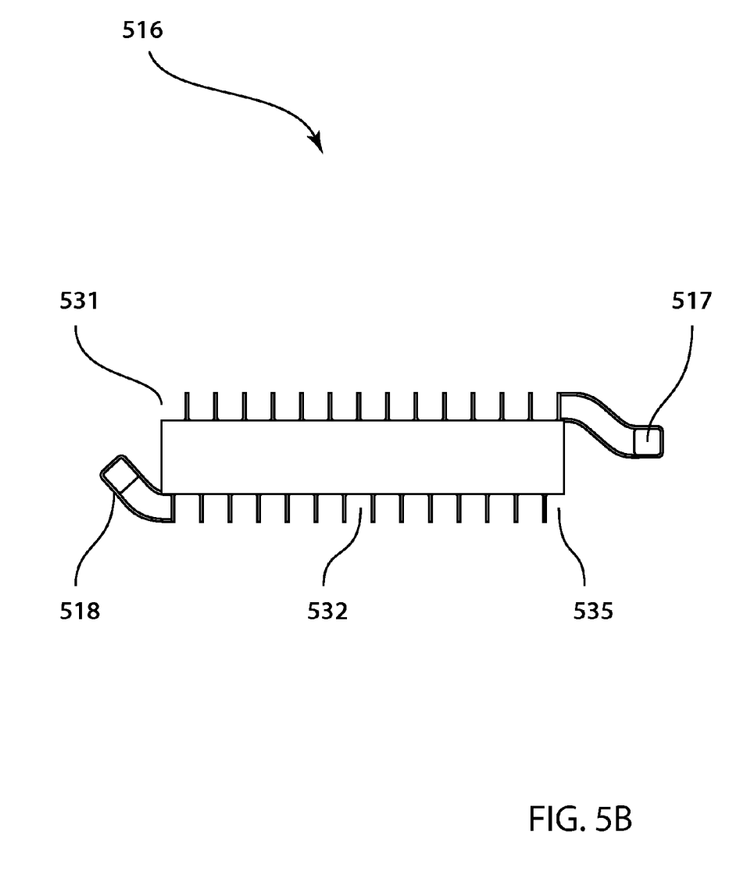
FIG. 5B is cross-sectional of the core of the cryosurgical instrument of FIG. 5A.

Referring to FIGS. 5A, and 5B, there is shown another non-limiting example of a cryosurgical instrument that is consistent with an exemplary embodiment of the present invention. Generally, the cryosurgical instrument 500 comprising a heat exchanger with a core 516 with a pair of helical grooves (threads) that direct a flow of cryogen, which is consistent with an exemplary embodiment of the present invention.

As shown, the cryosurgical instrument 500 includes a shaft 503 surrounding a double threaded core 516, and a tip 509 at the forward end of the cryosurgical instrument 500. The shaft 503 and the tip 509 generally define the exterior of the cryosurgical instrument 500.

At rear portion, the cryosurgical instrument 500 includes insulation 504 located on an internal surface of the external shaft 503. The insulation 504 separates the inner surface of the shaft 503 from a return flow 514 of cryogen exiting the cryosurgical instrument 500 so as to reduce any heat transfer therebetween. The rear portion also includes a cryogen inlet 502 through which cryogen is delivered to one thread of core 516.

The portion of the cryosurgical instrument from the tip 509 to the insulation 504 defines a cooling zone 505. This cooling zone 505 is a zone in which heat is exchanged between the cryogen and the cryoprobe. As a result, the freezing (ablation) of tissue occurs around the cooling zone 505, when the instrument is in operation and in contact with tissue.

The inlet 502 receives cryogen and delivers the received cryogen into the shaft 503 to the delivery thread 530 of the core 516. As explained above, the shaft 503 features insulation 504 that surrounds the shaft 503 and is mounted to the inner surface of the shaft 503. The insulation 504 is disposed outside of the cooling (heat exchange) zone 505. The presence of the insulation 504 ensures that freezing occurs only where treatment is desired, which is generally around the cooling zone 505.

The core 516, shown in FIG. 5B, with its double threads, fits tightly against the internal surface of the shaft 503, creating two separate spiral pathways (530 and 532). Preferably, the fit between the shaft 503 and the core 516 is an interference fit. A tight fit such as an interference fit results in the cooperation of the threads (530, 532) with the inner surface of the shaft 503 to yield respective cryogen pathways, which act as phase separators.

The core 516 is disposed lengthwise along a longitudinal or lengthwise axis of the cryosurgical instrument. For this reason, it is preferable that the core has a substantially cylindrical shape with a substantially circular cross-section. It is to be understood, however, that other cross-sectional shapes are both possible and contemplated. Also, it is preferable that the outside diameter of the core 516 threads, and the inner diameter of the shaft 503 are respectively uniform, so that there is no space between the core 516 and the shaft 503, except for the pathways. It is to be understood, however, that other shapes and non-uniform diameters are both possible and contemplated.

The cryogen is delivered via the delivery thread 530 of the core 516 to the tip 509. The delivery thread discharges the cryogen into at an expansion chamber 523 through open thread 530, as indicated by arrow 519. After boiling in the expansion space 523, the cryogen flows into the return thread 532, via inlet structure 518, which carries the cryogen from the cooling zone 505 to the open thread end 535 to flow into the return gap 507 as shown by arrow 513.

It is preferable that the core 516 fit tightly with the shaft 503 so that the tunnels generated by the double thread and the shaft 503 generates tight closed flow tunnels without mixing. This tight fit promotes temperature communication between the boiling cryogen and the shaft 503 in the cooling zone 505. It is to be understood, however, that the diameters need not be uniform or even the same. Further, it is to be understood that other shapes of the tubes are both possible and contemplated.

As a result, in operation, the respective threads of the core 516 provide two cryogen phase separators, as explained below. This results in effective temperature communication between the boiling cryogen flow in and out and the shaft 503.

Operation of the cryosurgical instrument 500 is discussed.

In operation, cryogen enters through the delivery 502, as indicated by arrow 514, and is directed to delivery thread 530, via inlet structure 517. This inflowing of cryogen then enters the threaded core 516 and flows in the helical pathway such that it spirals around as it travels toward the tip 509. This spinning of the inflowing cryogen causes the cryogen to at least partially separate into a liquid phase and a gaseous phase, with the heavier liquid phase tending to displace the gaseous phase along the inner surface of the delivery tunnel. As explained above, the delivery thread 530 delivers the cryogen to the tip 509. The return cryogen flows into the return thread 532, in the same spiral manner as the delivery cryogen flow, separating at least partially the liquid phase from the gaseous phase.

Thus, in operation, cryogen flows in the delivery pathway resulting from the delivery thread and the inner surface of the shaft 503, continues to the expansion space 523, enters the return pathway resulting from the return thread 535 and the inner surface of the shaft 503, leaves the cooling zone 505 to flow out of open thread end 535 as shown by arrow 513.

Figure 6:
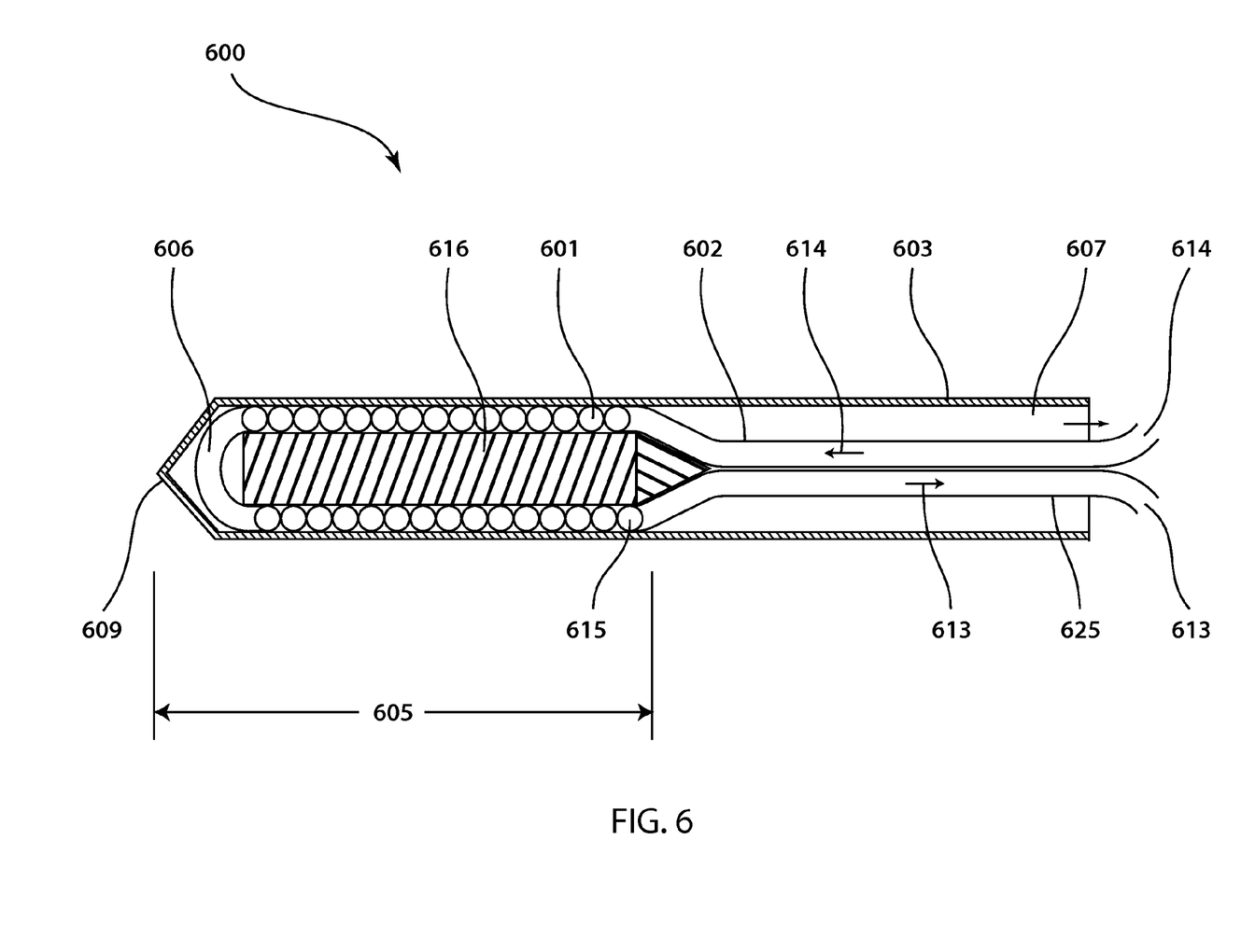
FIG. 6 is cross-sectional view of a non-limiting example of a cryosurgical instrument consistent with an exemplary embodiment of the present invention.

Referring to FIG. 6, there is shown a non-limiting example of a cryosurgical instrument comprising a heat exchanger that features multiple helical tubes, which is consistent with an exemplary embodiment of the present invention. Generally, the cryosurgical instrument 600 includes a cryogen return tube that extends beyond the shaft and passes through a negative pressurized gap that serves as insulation.

As shown, the cryosurgical instrument 600 includes a shaft 603 surrounding a cryogen inlet 602, a core 616, a cryogen delivery tube 601, and a tip 609 at the forward end of the cryosurgical instrument 600. The shaft 603 and the tip 609 generally define the exterior of the cryosurgical instrument 600.

At a rear portion, the gap 607 of the cryosurgical instrument 600 is continuously evacuated by vacuum pump or other source (not shown). The vacuum removes air, which conducts/transmits heat energy. By removing the air in the gap 607, the transmission of heat/cold is reduced. In this way, the low pressure/vacuum in the gap 607 yields an insulation effect between the shaft 603 and the return tube 625. The vacuum in the return gap 607 inhibits communication of temperature and in this way serves as insulation between the shaft 603 and the return tube 625. Stated differently, this vacuum separates the inner surface of the shaft 603 from a return flow 613 of cryogen exiting the cryosurgical instrument 600 so as to reduce any heat transfer there between. The presence of the vacuum in the gap promotes freezing only where treatment is desired, which is generally around the cooling zone 605.

The portion of the cryosurgical instrument from the tip 609 to the negative pressurized gap 607 defines a cooling zone 605. This cooling zone 605 is a zone in which heat is exchanged between the cryogen and the cryoprobe. As a result, the freezing (ablation) of tissue occurs around the cooling zone 605, when the instrument is in operation and in contact with tissue.

The inlet tube 602 receives cryogen and delivers the received cryogen into the shaft 603 to the delivery tube 601.

The core 616 is disposed lengthwise along a longitudinal or lengthwise axis of the cryosurgical instrument. For this reason, it is preferable that the core has a substantially cylindrical shape with a substantially circular cross-section. It is to be understood, however, that other cross-sectional shapes are both possible and contemplated. Also, it is preferable that the outside diameter of the core 616 and the inner diameter of the shaft 603 are respectively uniform, so that the space between the core 616 and the shaft 603 is uniform. It is to be understood, however, that other shapes and non-uniform diameters are both possible and contemplated.

The cryogen delivery tube 601 is arranged so as to substantially surround the core 616. To this end, the delivery tube 601 is helical and spirals around the core 616 from a distal end of the core 616 (relative to the tip 609) to the tip 609. The delivery tube 601 includes a bending 606 near the tip 609. At the bending 606, the delivery tube 601 transitions into the return tube 615 and changed direction by 180 degrees.

It is preferable that the delivery tube 601 and the return tube 615 fit tightly between the core 616 and the shaft 603 so that the tubes are in direct contact with the shaft 603. This tight fit promotes temperature communication between the tubes and the shaft 603 in the cooling zone 605. To encourage the tight fit, it is preferably that the delivery tube 601 and the return tube 615 share the same, uniform outside diameter. It is to be understood, however, that the diameters need not be uniform or even the same. Further, it is to be understood that other shapes of the tubes are both possible and contemplated.

It is to be appreciated that both the delivery tube 601 and the return tube 615 contemporaneously spiral around the core 616 in a cooperative manner such that respective windings of these tubes alternate, when the cryosurgical instrument 600 is viewed in cross-section as in FIG. 6. As a result, in operation, the respective windings interweave around the core 616 and provide two cryogen phase separators, as explained below. Also, the delivery tube 601 and the return tube 615 are in contact with the inner surface of the shaft 603 in at least the cooling zone 605. This results in effective temperature communication between the tubes and the shaft 603.

Operation of the cryosurgical instrument 600 is discussed.

In operation, cryogen enters through the inlet tube 602, as indicated by arrow 614, and is directed to delivery tube 601. This inflowing of cryogen then enters the delivery tube 601 and flows in the helical tube such that it spirals around the core 616 as it travels toward the tip 609. This spinning of the inflowing cryogen causes the cryogen to at least partially separate into a liquid phase and a gaseous phase, with the heavier liquid phase tending to displace the gaseous phase along the inner surface of the delivery tube 601. As explained above, the delivery tube 601 terminates at bend 606, where the flow changes direction 180 degrees. The return flow, indicated by arrow 613, flows in the return tube 615. This spinning of the exhaust cryogen further encourages the cryogen to separate into a liquid phase and a gaseous phase, with the heavier liquid phase tending to displace the gaseous phase along the inner surface of the return tube 615.

Thus, in operation, cryogen flows in the delivery tube 601, continues directly to return tube 615 via the bend 606, and leaves the cooling zone 605 to flow out of the return tube 615 into the return tube 625, as shown by arrow 613. Bend 606 is optionally placed close to the inner surface of tip 609. It is to be understood, however, that the tip 609 need not be hollow. Also, it is preferable that the bending 606 of the delivery tube tube 601 be as close as possible to the inner surface of the tip 609.

More specifically, the inflowing cryogen (indicated by arrow 614) boils continuously as it flows in the delivery tube 601, the bend 606, and the return tube 615 until it flows out via return tube 625, shown by arrow 613. The return flow of exhausted cryogen leaves the cooling zone 605 and continues as the return flow 613, as shown.

Figure 7:
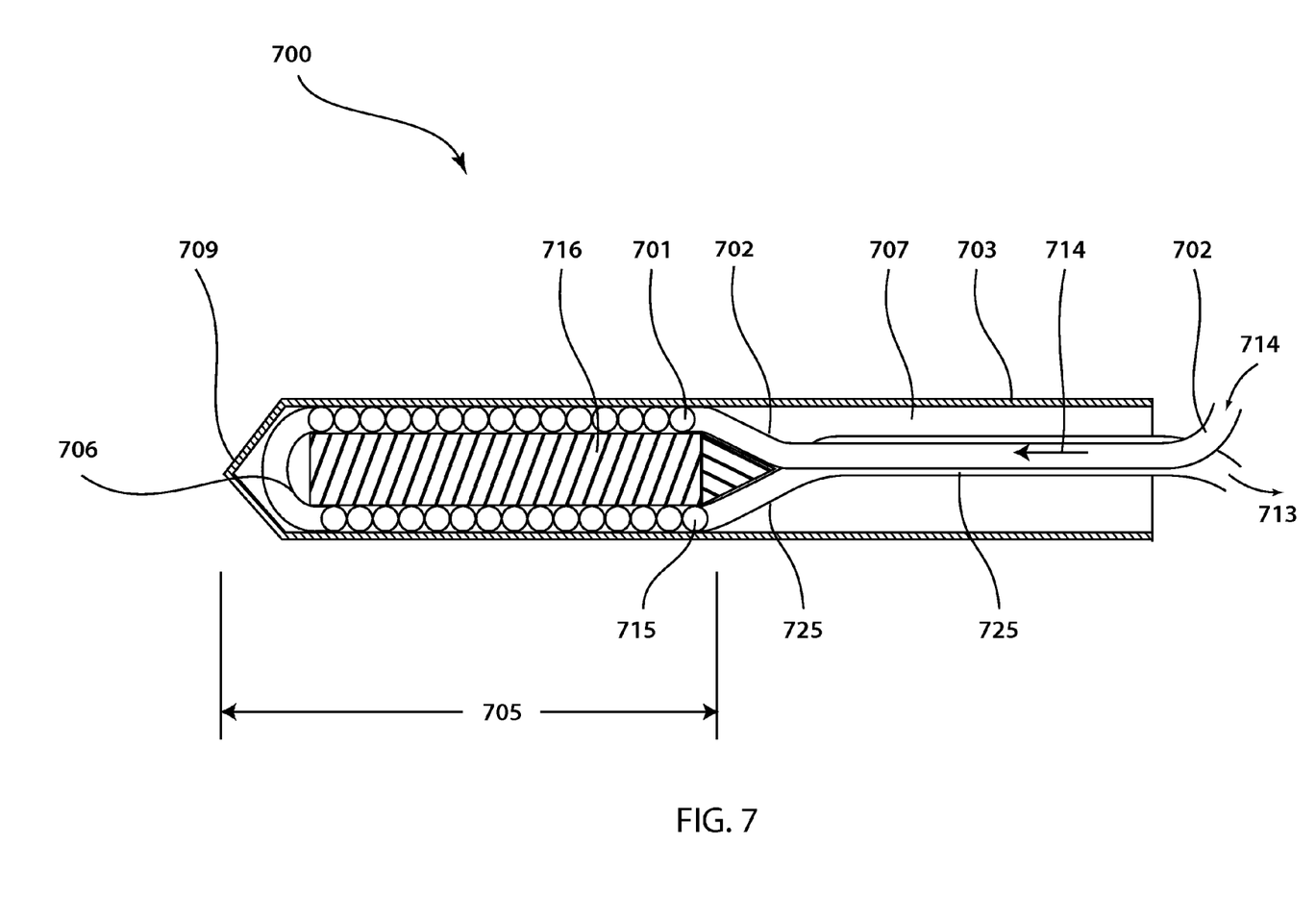
FIG. 7 is cross-sectional view of a non-limiting example of a cryosurgical instrument consistent with an exemplary embodiment of the present invention.

Referring to FIG. 7, there is shown a non-limiting example of a cryosurgical instrument comprising a heat exchanger that features multiple helical tubes, which is consistent with an exemplary embodiment of the present invention. Generally, the cryosurgical instrument 700 includes a cryogen return tube that extends beyond the shaft, passes through a negative pressurized gap that serves as insulation, and surrounds a cryogen inlet tube 702. Also, a portion of the cryogen delivery tube is disposed within the cryogen return tube.

As shown, the cryosurgical instrument 700 includes a shaft 703 surrounding a cryogen inlet tube 702, a core 716, a cryogen delivery tube 701, and a tip 709 at the forward end of the cryosurgical instrument 700. The shaft 703 and the tip 709 generally define the exterior of the cryosurgical instrument 700.

At a rear portion, the gap 707 of the cryosurgical instrument 700 is continuously evacuated by vacuum pump or other source (not shown). The vacuum removes gaseous nitrogen, which conducts/transmits heat energy. By removing the air in the gap 707, the transmission of heat/cold is reduced. In this way, the low pressure/vacuum in the gap 707 yields an insulation effect between the shaft 703 and the return tube 725. The vacuum in the return gap 707 inhibits communication of temperature and in this way serves as insulation between the shaft 703 and the return tube 725. Stated differently, this vacuum separates the inner surface of the shaft 703 from a return flow 713 of cryogen exiting the cryosurgical instrument 700 so as to reduce any heat transfer there between. The presence of the vacuum in the gap promotes freezing only where treatment is desired, which is generally around the cooling zone 705.

The portion of the cryosurgical instrument from the tip 709 to the negative pressurized gap 707 defines a cooling zone 705. This cooling zone 705 is a zone in which heat is exchanged between the cryogen and the cryoprobe. As a result, the freezing (ablation) of tissue occurs around the cooling zone 705, when the instrument is in operation and in contact with tissue.

The inlet tube 702, placed inside of the return tube 725, receives cryogen and delivers the received cryogen into the delivery tube 701.

The core 716 is disposed lengthwise along a longitudinal or lengthwise axis of the cryosurgical instrument. For this reason, it is preferable that the core has a substantially cylindrical shape with a substantially circular cross-section. It is to be understood, however, that other cross-sectional shapes are both possible and contemplated. Also, it is preferable that the outside diameter of the core 716 and the inner diameter of the shaft 703 are respectively uniform, so that the space between the core 716 and the shaft 703 is uniform. It is to be understood, however, that other shapes and non-uniform diameters are both possible and contemplated.

The cryogen delivery tube 701 is arranged so as to substantially surround the core 716. To this end, the delivery tube 701 is helical and spirals around the core 716 from a distal end of the core 716 (relative to the tip 709) to the tip 709. The delivery tube 701 includes a bending 706 near the tip 709. At the bending 706, the delivery tube 701 transitions into the return tube 715 and changed direction by 180 degrees.

It is preferable that the delivery tube 701 and the return tube 715 fit tightly between the core 716 and the shaft 703 so that the tubes are in direct contact with the shaft 703. This tight fit promotes temperature communication between the tubes and the shaft 703 in the cooling zone 705. To encourage the tight fit, it is preferably that the delivery tube 701 and the return tube 715 share the same, uniform outside diameter. It is to be understood, however, that the diameters need not be uniform or even the same. Further, it is to be understood that other shapes of the tubes are both possible and contemplated.

It is to be appreciated that both the delivery tube 701 and the return tube 715 contemporaneously spiral around the core 716 in a cooperative manner such that respective windings of these tubes alternate, when the cryosurgical instrument 700 is viewed in cross-section as in FIG. 7. As a result, in operation, the respective windings interweave around the core 716 and provide two cryogen phase separators, as explained below. Also, the delivery tube 701 and the return tube 715 are in contact with the inner surface of the shaft 703 in at least the cooling zone 705. This results in effective temperature communication between the tubes and the shaft 703.

Operation of the cryosurgical device 700 is discussed.

In operation, cryogen enters through the inlet tube 702, as indicated by arrow 714, and is directed to delivery tube 701. This inflowing of cryogen then enters the delivery tube 701 and flows in the helical tube such that it spirals around the core 716 as it travels toward the tip 709. This spinning of the inflowing cryogen causes the cryogen to at least partially separate into a liquid phase and a gaseous phase, with the heavier liquid phase tending to displace the gaseous phase along the inner surface of the delivery tube 701. As explained above, the delivery tube 701 bends (706) 180 degrees and is in the gap between the delivery tube 701 to create the return tube 715, and the cryogen flow into return tube 725, placed inside vacuum pressure in the shaft 703. The return flow, indicated by arrow 713, flows in the return tube 725. This spinning of the exhaust cryogen further encourages the cryogen to separate into a liquid phase and a gaseous phase, with the heavier liquid phase tending to displace the gaseous phase along the inner surface of the return tube 715.

Thus, in operation, cryogen flows in the delivery tube 701, continues directly to return tube 715 via the bend 706, and leaves the cooling zone 705 to flow out of the return tube 715 into the return tube 725, as shown by arrow 713. Bend 706 is optionally placed close to the inner surface of tip 709. It is to be understood, however, that the tip 709 need not be hollow. Also, it is preferable that the bending 706 of the delivery tube 701 be as close as possible to the inner surface of the tip 709.

More specifically, the inflowing cryogen (indicated by arrow 714) boils continuously as it flows in the delivery tube 701, the bend 706, and the return tube 715 until it flows out via the return tube 725, shown by arrow 713. The return flow of exhausted cryogen leaves the cooling zone 705 and continues as the return flow 713, as shown.

It is to be appreciated that various materials of the various components of the cryosurgical instruments may be selected so that the cryosurgical instruments are flexible, or at least partially flexible. Also, it is to be appreciated that this flexibility makes it possible to travel with the cryosurgical instrument within a body in, for example, a blood vessel. This flexibility is contemplated for the cryosurgical instruments 600 and 700.

In the context of cardiac care, cryoablation can be used to various conditions. For example, cryotherapy is effective in treating cardiac arrhythmias by freezing the cardiac tissue or pathways that interfere with the normal distribution of the heart's electrical impulses. This restores normal electrical conduction. In a catheterization procedure, a flexible cryocatheter is inserted into a blood vessel and threaded to the heart where it delivers cold. In surgical procedure, a flexible probe is used directly on an exposed heart to apply the cold that interrupts the arrhythmia.

Also, in the context of cardiac care, cryoablation can be used in diagnostics. For example, cryotherapy is effective in mapping. In cryomapping cold temporarily chills conducting tissue in the target area, creating a reversible electrical effect. This allows for precise site testing and confirmation prior to proceeding with definitive ablation.

Still further, flexible cryosurgical instruments and cryocatheters can be desirable in treatments in various organs and cavities of a patient, including uterine fertility treatments and ablations in the bladder, prostate and breast.

As the foregoing detailed description illustrates, an aspect of the present invention yields a heat exchanger that advantageously uses centrifugal force to separate an exhaust flow of cryogen into two phases by spinning a flow of cryogen within a helical/spiral coil. This spiraling urges the heavier liquid phase of the exhaust cryogen against the inner surface of the shaft, which encourages enhanced cooling in the cooling zone since the liquid phase has a higher heat capacity (i.e. thermal capacity) than the gaseous phase. Additionally, the incoming flow of cryogen, which is delivered via a helical coil, also spins and tends to separate into liquid and gaseous phases.

As the foregoing also illustrates, the spiraling flow of the exhausted cryogen is achieved by forming cryogen delivery and return tubes with helical portions that spiral around and contact the solid core element. Also, spacing between the coils of the helical portions can be used to form a spiraling pathway.

Still further, it is to be appreciated that the phase separation that occurs may occur during cryogen delivery and/or during cryogen exhaust. It may be partial, substantially complete, or complete. Indeed, it may be partial during delivery and completed during exhaust. Also, it is to be appreciated that the amount of phase separation during delivery may be the same or different than the amount of phase separation during exhaust.

Examples of various features/aspects/components/operations have been provided to facilitate understanding of the disclosed embodiments of the present invention. In addition, various preferences have been discussed to facilitate understanding of the disclosed embodiments of the present invention. It is to be understood that all examples and preferences disclosed herein are intended to be non-limiting.

Although selected embodiments of the present invention have been shown and described individually, it is to be understood that at least aspects of the described embodiments may be combined. Although selected embodiments of the present invention have been shown and described, it is to be understood the present invention is not limited to the described embodiments. Instead, it is to be appreciated that changes may be made to these embodiments without departing from the principles and spirit of the invention, the scope of which is defined by the claims and the equivalents thereof.

What is claimed is:

1. A cryosurgical instrument comprising:
a shaft having a pointed distal end and a proximal end adapted and configured to receive an inflow of cryogen and to exhaust a flow of expanded cryogen;
a core disposed within the shaft;
a cryogen delivery tube having a helical portion that spirals around the core, the delivery tube configured to deliver a received flow of cryogen to a downstream end near the pointed distal end of the shaft; and
a cryogen return tube having a helical portion that spirals around the core, the return tube configured to accept, at an upstream end thereof near the distal pointed end of the shaft, a return flow of cryogen,
wherein the helical portions of the tubes are in fluid tight contact with the core and an inner surface of the shaft,
wherein the helical portions of the tubes spiral about the core in an alternating arrangement such that they alternate along a length of the core, and
wherein the core and the helical portions of the delivery tube and the return tube comprise a centrifugal phase separator.

2. The cryosurgical instrument 1, wherein the downstream end of the delivery tube and the upstream end of the return tube are interconnected by a bend disposed proximate to an inner side of the pointed distal end of the shaft.

3. The cryosurgical instrument of claim 1, wherein the helical portions of the tubes spiral only in an ablation zone.

4. The cryosurgical instrument of claim 1, wherein the core is disposed lengthwise along a lengthwise axis of the cryosurgical instrument.

5. The cryosurgical instrument of claim 1, wherein the core has a substantially cylindrical shape with a substantially circular cross-section.

6. The cryosurgical instrument of claim 1, wherein the core is solid.

7. The cryosurgical instrument of claim 1, wherein an outside diameter of the core and an inner diameter of the shaft are respectively uniform and a space between the core and the shaft is uniform.

8. The cryosurgical instrument of claim 1, wherein the helical portions of the tubes both have a respective rectangular cross-section.

9. The cryosurgical instrument of claim 1, wherein the helical portions of the tubes spin cryogen flowing therethrough so as to promote phase separation of the cryogen.

10. The cryosurgical instrument of claim 1, wherein a portion of the cryosurgical instrument within the shaft, adjacent to the core and opposite the pointed distal end of the shaft, comprises a vacuum chamber,
wherein the delivery tube includes a non-helical portion upstream from the helical portion thereof,
wherein the return tube includes a non-helical portion downstream from the helical portion thereof, and
wherein the non-helical portions of the tubes extend within the vacuum chamber.

11. The cryosurgical instrument of claim 10, wherein a part of the non-helical portion of the delivery tube is disposed in a portion of the non-helical portion of the return tube.

12. A cryosurgical instrument comprising:
a shaft having a pointed distal end and a proximal end adapted and configured to receive an inflow of cryogen and to exhaust a flow of expanded cryogen;
a core disposed within the shaft;
a cryogen delivery tube having a helical portion that spirals around the core and delivers a flow of cryogen toward the pointed distal end of the shaft, the delivery tube being in fluid tight contact with the core and an inner surface of the shaft; and
a cryogen return tube having a helical portion that spirals around the core, the return tube configured to accept, at an upstream end thereof near the distal pointed end of the shaft, a return flow of cryogen,
wherein the respective spirals of the helical portions of the tubes are respectively spaced,
wherein the helical portions spin a cryogen flowing therethrough so as to promote phase separation of the cryogen,
wherein the spaced spirals of the helical portions of the tubes, the core, and the inner surface of the shaft cooperate so as to form a spiraling cryogen return pathway that spins a cryogen flowing therethrough so as to promote phase separation of a flow cryogen therethrough, and
wherein expanded cryogen may be exhausted via the return tube or the return pathway.

13. The cryosurgical instrument of claim 12, wherein the helical portion of the cryogen delivery tube has a rectangular cross-section.

14. A cryosurgical instrument, comprising:
a shaft having a pointed distal end and a proximal end adapted and configured to receive an inflow of cryogen and to exhaust a flow of expanded cryogen; and
a core disposed within the shaft and in fluid tight contact with an inner surface of the shaft, the core having two exterior spiraling threads that cooperate with the inner surface of the shaft to form first and second respective spiraling pathways, a first spiraling pathway being a cryogen delivery pathway, the second spiraling pathway being a cryogen return pathway,
wherein the cryogen delivery pathway is configured to deliver a received flow of cryogen to a downstream end near the pointed distal end, and
wherein the cryogen return pathway is configured to accept, at an upstream end thereof, a return flow of cryogen from the distal pointed end.

* * * * *